United States Patent
Owiesy

(10) Patent No.: US 9,775,850 B2
(45) Date of Patent: Oct. 3, 2017

(54) COMPOSITION AND METHOD FOR CURING MIGRAINE HEADACHES

(71) Applicant: Faro Owiesy, Corona, CA (US)

(72) Inventor: Faro Owiesy, Corona, CA (US)

( * ) Notice: Subject to any disclaimer, the term of this patent is extended or adjusted under 35 U.S.C. 154(b) by 0 days.

(21) Appl. No.: 15/277,439

(22) Filed: Sep. 27, 2016

(65) Prior Publication Data

US 2017/0014427 A1    Jan. 19, 2017

Related U.S. Application Data

(62) Division of application No. 14/167,915, filed on Jan. 29, 2014, now abandoned.

(51) Int. Cl.
| | |
|---|---|
| *A61K 31/167* | (2006.01) |
| *A61K 31/51* | (2006.01) |
| *A61K 31/662* | (2006.01) |
| *A61K 31/573* | (2006.01) |

(52) U.S. Cl.
CPC .......... *A61K 31/573* (2013.01); *A61K 31/167* (2013.01); *A61K 31/51* (2013.01); *A61K 31/662* (2013.01)

(58) Field of Classification Search
CPC .... A61K 31/573; A61K 31/51; A61K 31/167; A61K 31/662
USPC .................................................. 514/120, 171
See application file for complete search history.

(56) References Cited

U.S. PATENT DOCUMENTS

| | | |
|---|---|---|
| 4,866,050 A | 9/1989 | Ben-Amoz |
| 5,855,907 A | 1/1999 | Peyman |
| 6,106,819 A | 8/2000 | Sucher |
| 8,450,379 B2 | 5/2013 | Belanoff |

FOREIGN PATENT DOCUMENTS

| | | |
|---|---|---|
| MX | PA01006567 | 1/2003 |
| WO | WO2011042701 A1 | 4/2011 |
| WO | WO2013016332 A3 | 7/2013 |

OTHER PUBLICATIONS

Singh, "Does the addition of dexamethasone to standard therapy for acute migraine headache decrease the incidence of recurrent headache for patients treated in the emergency department? A meta-analysis and systematic review of the literature" (Dec. 2008;15(12):1223-33) Journal Academic Emergency Medicine.
Caram-Salas, "Thiamine and Cyanocobalamin Relieve Neuropathic Pain in Rats: Synergy with Dexamethasone" (2006; 77:53-62) Pharmacology.
Office Action of Parent U.S. Appl. No. 14/167,915.
Joo et al., Lidocaine suppresses the increased extracellular signal-regulated kinase/cyclic AMP response element-binding protein pathway and pro-inflammatory cytokines in a neuropathic pain model of rats. (2011); Eur J Anaesthesiol Feb. 2011; 28(2):106-11.
Braaf, "Migraine headaceh: an analysis of 124 cases treated by head-traction manipulation and thiamin chrloride." N.Y. State, J.M Migraine Headache Feb. 15, 1951, pp. 528-533.

*Primary Examiner* — Jennifer M Kim
(74) *Attorney, Agent, or Firm* — Trojan Law Offices

(57) ABSTRACT

The invention is directed to methods and compositions for curing migraine headaches. In particular, compositions are described involving the combination of dexamethasone, lidocaine, and thiamine. The methods of curing a patient of migraines having trigeminal or occipital neuralgia involves administering, by subcutaneous injection during a single treatment session, a combination of dexamethasone, lidocaine and thiamine to several craniofacial nerves.

13 Claims, No Drawings

COMPOSITION AND METHOD FOR CURING MIGRAINE HEADACHES

CROSS REFERENCE TO RELATED APPLICATIONS

This application is a divisional of U.S. patent application Ser. No. 14/167,915, filed on Jan. 29, 2014, which is hereby incorporated by reference in its entirety.

FIELD OF THE INVENTION

The present invention relates to a composition and method for the cure of recurring migraine headaches. In particular, the composition and method involves the administration of a combination of dexamethasone, lidocaine, and thiamine to a patient.

BACKGROUND OF THE INVENTION

Migraine headaches are an episodic neurovascular disorder characterized by recurrent unilateral headaches often accompanied by nausea, vomiting, photophobia, phonophobia, conjuctival injection, lacrimation, dysthesia/hypothesia of the tongue, TMJ pain, and/or dental pain. Migraines are a common and potentially serious chronic disabling disease. Recurring migraines often lead to a pattern of depression, anxiety, generalized phobia, and other nonspecific mood disorders. The prevalence of migraines in the U.S. adult population is roughly 20% among women and 9% among men. This equates to approximately 30 million American adults who suffer from migraine headaches, and data show that about one half of migraine headaches produce severe impairment that force an individual to bed rest. These numbers translate into millions of bedridden days per year, and produce a financial burden on individuals and businesses due to missed workdays, which have been estimated at about $14 billion annually.

Despite the severity and commonplaceness of migraines headaches in the population, the exact pathogenesis of migraine headaches remains unknown. Factors such as bright lights, ultraviolet waves, flickering lights, as well as certain visual patterns, smells, noises, or tastes, may trigger migraine headaches. Visual cortical hyperexcitability may be responsible for migraines and life stressors may also trigger a migraine attack.

The dynamic of the migraine attack, with its broad range of manifestations, has given rise to several scientific and nonscientific hypotheses and theories. Most of these theories still need to be rigorously and scientifically tested. The general hypothesis for the etiology of migraine headaches suggests that the initiation of a migraine attack involves a primary event in the central nervous system (CNS), probably involving a combination of genetic expression changes in ion channels, and environmental changes, which render an individual more sensitive to environmental factors. These physiological changes may in turn result in a wave of cortical spreading when the attack is initiated. Other hypotheses suggest that migraines are a complex familial disorder in which the severity and the susceptibility of individuals are most likely governed by several genes that vary between families. However, most of these theories lack the studies to prove their hypotheses.

Known migraine treatments have included agents capable of inhibiting the biological action of the glucocorticoid receptor, such as dexamethasone. One example of a dexamethasone treatment is taught by Belanoff in U.S. Pat. No. 8,450,379. However, the use of dexamethasone as a treatment has been shown to be limited. Singh et al. found only a modest benefit (a 9.7% risk reduction) from the use of dexamethasone when dexamethasone was added to a standard migraine treatment. (Journal Academic Emergency Medicine, "Does the addition of dexamethasone to standard therapy for acute migraine headache decrease the incidence of recurrent headache for patients treated in the emergency department? A meta-analysis and systematic review of the literature" by Singh (2008 December; 15(12):1223-33)). This study and others have shown that current dexamethasone treatment methods produce only modest effects in their ability to reduce long-term recurrence of migraines.

While the use of corticosteroids, such as dexamethasone, can be beneficial in the clinical setting of acute craniofacial neuralgia, chronic use of corticosteroids may have many adverse side effects, such as increased pain, infection, shrinking of soft tissue, and loss of color in the skin. Due to the side effects from injected corticosteroids, many physicians limit corticosteroid injections to no more than three or four injections per year. Therefore, the long-term benefits of the use of corticosteroids for migraine treatment is limited by the adverse effects of continuous corticosteroid treatment. Therefore it would be advantageous to develop compositions and methods for treating migraines that utilize short-term corticosteroid treatments, but still produce long-term results.

Another treatment method for migraines includes the use intranasal or ocular applications of an anesthetic such as lidocaine. In U.S. Pat. No. 6,106,819, Sucher discloses the use of lidocaine drops to treat migraines. However, lidocaine treatment methods have also yielded only modest short-term results.

Migraines headaches have also been treated by ingestion of thiamine, as taught by Green in PCT Application No. WO/2013/016332, with modest effects. The above-mentioned agents (dexamethasone, lidocaine, and thiamine), when taken alone, and by using current administration methods, have not proven effective for curing migraines, or even for long-term relief from migraine headaches.

Combinations of the above mentioned agents have been shown to have positive effects on subjects with neurological problems. For example, the combination of thiamine and dexamethasone were cited in a study by Caram-Salas et al., in PCT Patent Application No. WO/2011/042701 to Valayer, where the co-administration of thiamine or cyanocobalamin, and dexamethasone, reduced spinal nerve ligation induced allodynia, showing a synergistic effect between either thiamine or cyanocobalamin and dexamethasone.

U.S. Pat. No. 5,855,907 to Peyman discloses methods of treating a migraine comprising the topical administration of an anesthetic (such as lidocaine) in combination with anti-inflammatory compounds including dexamethasone. However, Peyman teaches that the use lidocaine was effective in only about 55% of patients, and there was no evidence of long-term reduction of migraines.

Therefore, there remains a need for improved long-lasting migraine headache treatment methods and compositions.

SUMMARY OF THE INVENTION

The invention relates to a cure of migraine headaches and the associated symptoms. Broadly, the invention is a combination of dexamethasone, lidocaine, and thiamine, administered by injection at several locations in proximity to branches of the trigeminal nerve and/or branches of the occipital nerve, in order to eliminate the recurrence of migraine headaches. In one embodiment, composition comprises dexamethasone, lidocaine, and thiamine, and in another embodiment, the composition consists of the active pharmaceutical ingredients of dexamethasone, lidocaine, and thiamine.

To understand the empiric treatment and satisfactory long-term results for the elimination of migraine headaches, a proper understanding of the molecular biological mechanism of the autonomous nervous system is crucial. Key to this understanding is that a headaches have an etiology based on a malfunction of the sympathetic and parasympathetic (autonomous) nervous systems on a cellular basis.

The autonomous nervous system is an independent, self-managed, and self-controlled system serving a complex multifunctional internal system of organs. The autonomous nervous system function continues even when the cognitive cerebral centers are out of function. The autonomous nervous system demonstrates the dual function of the pro and contra functioning systems called the sympathetic and parasympathetic nervous systems.

The compositions and treatments methods in this invention were deduced from the hypothesis that migraines are the result of an imbalance between sympathetic and parasympathetic innervation of the cerebrovascular system caused by a dysbalance of vascular supply, and an inflammatory mechanism of nerve cells, rather than the commonly accepted general hypothesis of a central cortical cause of migraines.

A better explanation than the generally accepted central cortical cause of migraines is that migraines are a result of chronic periodic vasoconstriction in ganglia and the associated peripheral nerves, which are predilections to anoxia/hypoxia (diminished oxygenation) and consequent acute inflammatory reactions, possibly neuritis and perineuritis in the nerve endings. Acute or periodic inflammatory responses lead to the release of inflammatory neuropeptides, which cause additional vasoconstriction in the nerve branch supplies, irritating Schwan cells of the perineurium/epineurium by anoxic/hypoxic reactions.

Long-term prevention, and even total elimination of the inflammatory response may be accomplished by the administration of dexamethasone, lidocaine, and thiamine in calculated proportions in proximity to the trigeminal and/or occipital nerve divisions and branches.

In the present invention, one embodiment that eliminates the continued long-term treatment of corticosteroids is the combination of dexamethasone with lidocaine and thiamine. In particular, dexamethasone phosphate used with lidocaine and thiamine silences/desilences biological switches of the parasympathetic and sympathetic nervous system, and balance the sympathetic and parasympathetic stimulatory effect of the perivascular autonomic nervous system. Accordingly, in one aspect of the invention, there exists a pharmaceutical composition for curing migraine headaches by administering a combination, in a single treatment session of dexamethasone, lidocaine, and thiamine. The combination of all three of individual compositions of dexamethasone, lidocaine, and thiamine are more effective and produce longer lasting results than any one composition, or a combination of two of the three compositions.

The compositions and methods described herein have been found to be effective as a preventative treatment and long-term cure of recurring migraines. The combination of the correct dosage of active ingredients, together with the correct route of administration for these compositions results in the cure of migraines.

Dexamethasone phosphate is a synthetic glucocorticosteriod (a type of corticosteroid). It is a white to practically white, odorless, crystalline powder. It is stable in air and practically insoluble in water. Dexamethasone phosphate may aid in the prevention of migraines via the glucocorticoid response element (GRE). The GRE is a short sequence of DNA within the promoter of a gene that is able to bind to a specific glucocorticoid receptor complex, thereby regulating transcription of genes responsible for inflammation. Specifically, dexamethasone regulates the expression of COX-2, an inducible enzyme abundant at sites of inflammation. Dexamethasone may reduce migraine headaches and craniofacial neuralgia through nitric oxide-mediated vascular protection of hypoxic nerve cells, thereby inducing genetic expressive inhibition of COX-2, and nearly all pro-inflammatory cytokine-genes that lead to migraine headaches.

In one aspect of the composition, the amount of each ingredient per treatment session is about 12 mg dexamethasone phosphate, about 60 mg lidocaine, and about 100 mg thiamine. The total dose to a patient is administered in proximity to several craniofacial nerves during a single treatment session.

The invention is also directed to a method of prophylactically treating or curing the recurrence of migraine headaches by administering in proximity to the trigeminal or occipital nerve of a patient, a pharmaceutical composition having dexamethasone, lidocaine, and thiamine. The amount to be administered should be sufficient to reduce or eliminate the frequency of migraine relapse in patients or produce longer lasting efficacy compared to the administration of any one or two of these compositions, absent any of the other active compositions.

In one aspect of the invention, the composition is administered subcutaneously to the nerve branches of the trigeminal nerve and/or the greater and lesser occipital nerves, which rapidly provides relief. The composition reaches the nerve branches and parasympathetic cranial ganglia by direct diffusion. Understanding the communication between the branches between the parasympathetic ganglia, nerve branches of the trigeminal nerve, as well as the facial nerves is key to understanding the cure for migraine headaches. Furthermore, knowledge of the greater and lesser occipital nerve and it relationship to several rami communicantes of second, third and fourth cervical nerves aids in determining the correct location of where administration of the composition should occur since electrical discharges during a migraine attack propagate through the communicating branches of the greater occipital and lesser occipital nerves to the second, third, and fourth cervical nerves, which then stimulate the responsible muscle and muscle groups with contraction.

In one aspect of the invention, the patient is cured of migraine headaches after a single administration the pharmaceutical composition. A second treatment may be necessary for some patients that not fully responsive to the first treatment. A patient may be cured of migraines after a second treatment session by administering a second dose of the pharmaceutical composition. In one aspect of the method of treating migraines, the patient is treated by the simultaneous (i.e. during the same treatment session) administration of dexamethasone, lidocaine, and thiamine in calculated proportions, in proximity to the trigeminal nerve divisions and branches, and in proximity to the greater and lesser occipital nerves by injection.

Although compositions and materials similar or equivalent to those described herein can be used in the practice or testing of the present invention, suitable methods and materials are described below. All publications, patent applications, and patents mentioned herein are incorporated by reference in their entirety. In the case of conflict, the present specification, including definitions, will control. The particular embodiments discussed below are illustrative only and not intended to be limiting.

DETAILED DESCRIPTION OF THE INVENTION

It has been discovered that a combination of dexamethasone, lidocaine, and thiamine substantially reduces, or eliminates completely, the recurrence of migraine headaches. The invention encompasses compositions including dexamethasone, lidocaine, and thiamine, for preventing and/or curing migraine headaches and symptoms associated with migraines. Previous methods of using dexamethasone, lidocaine, and thiamine as individual compositions to reduce migraines have only provided modest or short-term relief from migraines. The compositions in the present invention not only reduce short-term migraine recurrence, but cure migraine headaches.

Migraine pain occurs in craniofacial nerves when these nerves lack oxygen and glucose, leading to downstream biochemical pathways that eventually induce severe pain. This pain is likely an evolutionary defense, a mechanism designed for the body to react to a decrease in oxygen and glucose in the nerves. With that in mind, Lidocaine serves the primary purpose of vasodilating (opening up) blood vessels around the nerve, and dexamethasone serves primarily as an anti-inflammatory agent. However, the use of just these two compositions is often not satisfactory, and the inclusion of thiamine into the formulation increases effectiveness by increasing the parasympathetic response, relaxing the muscles, and bringing the sympathetic and parasympathetic nerve systems into balance.

Thiamine was added to the formulation to increase efficacy due its possible role that thiamine might have in the long-term regulation of ribo-switches (i.e., its ability regulate mRNA molecules that bind to small molecules and affect protein synthesis). Specifically, the biosynthetic pathways of thiamine are regulated by ribo-switches. If there is sufficient thiamine present in the cell then thiamine binds to mRNA encoding genes required in the pathway that synthesizes thiamine, thus preventing translation of enzymes involved in thiamine biosynthesis.

Thiamine may be a key composition in the regulation of this switch because thiamine is a co-factor of transketolase and also regulates the enzyme pyruvate dehydrogenase. Transketolase is a key cytosolic enzyme involved in the pentose phosphate pathway, a major route for the biosynthesis of pentose sugars deoxyribose and ribose. In the nervous system, pyruvate dehydrogenase is also involved in the production of acetylcholine, a neurotransmitter, and for myelin synthesis. Thus, the addition of thiamine to a formulation having dexamethasone and lidocaine would increase potency of dexamethasone and lidocaine through direct diffusion in the nerve body by regulating the expression of genes that allow more oxygen and glucose to enter the nerve cells, which prevents inflammation, thereby preventing migraine headaches.

The presence of thiamine prevents the translation of enzymes responsible for thiamine biosynthesis such as such as transketolase and pyruvate dehydrogenase. Transketolase connects the pentose phosphate pathway to glycolysis, while pyruvate dehydrogenase contributes to linking glycolysis to the citric acid cycle as well as being involved in the production of acetylcholine, a neurotransmitter, and for myelin synthesis, which are involved the regulation of pro-inflammatory cytokines. Inflammation also leads arterial spastic function, which a hypoxia and/or anoxia in the branches of the trigeminal nerve, as well as in the occipital nerve, which leads to migraine headaches. Furthermore, thiamine pyrophosphate (TPP), a derivative of thiamine, is a co-enzyme in several enzymatic reactions and may also have a non-co-enzymatic function during stimulation of neuronal cells and other excitable tissues. It has been shown that if thiamine is present in the cells, thiamine binds to the mRNA encoding genes required in the TPP pathway, and thus, a treatment including thiamine causes downstream biochemical responses to change the genetic expression of nearly all pro-inflammatory cytokines genes (such as COX-2), and acts as a bio switch of the parasympathetic/sympathetic nervous system. The hypothesis is that once the parasympathetic and sympathetic nervous systems are into balance, the migraine may be cured and it is the long-term reduced expression of enzymes in these inflammatory pathways that likely prevent the long-term recurrence of migraines.

Treatment methods and compositions that use combination of dexamethasone, lidocaine, and thiamine have shown the following advantages over other migraine treatment methods and compositions: (1) a lower dose of lidocaine is required per treatment session, (2) fewer painful injection sites are necessary, (3) fewer reported remittance and relapses of migraine headaches, (4) patients report a reduced number of non-migrainous, e.g. tension headache experiences, (5) the treatment is a fairly non-aggressive approach that requires minimal dosage of medications, (6) the treatment has no major adverse reactions or contraindications, (7) patients of all ages and patients with comorbidities can accept treatment, (8) treatment is an ambulatory procedure requiring no costly preparation, (9) the treatment is extremely cost effective for patients, insurance, clinicians, (10) young and old patients have a high tolerance of this treatment compared to other treatment methods, (11) the patient has little or no need for maintenance medications or life style modifications after the treatment, and (12) the patient has a long lasting pain-free period, consistent with the treatment method being categorized as a cure.

As used herein, "Cure" as to migraine headaches, shall mean that no aggressive measures of continued use of migraine medications is needed over a period of about two years or longer.

As used herein, "Therapeutically effect amount" as to drug dosage shall mean a dosage that provides the specific pharmacological response for which the drug is administered in a significant number of subjects in need of such treatment. It is emphasized that headaches are not well understood and the etiologies of particular headaches will vary, as does the response to particular drugs. Thus, reference to "specific pharmacological response for which the drug is administered in a significant number of subjects in need of such treatment" is a recognition that a "therapeutically effective amount" administered to a particular subject in a particular instance may not abort the onset of a headache or relieve headache pain, even though such dosage is deemed a "therapeutically effective amount" by those skilled in the art.

In a preferred embodiment, each ml of dexamethasone phosphate contains dexamethasone sodium phosphate equivalent to dexamethasone phosphate 4 mg or, dexamethasone 3.33 mg; benzyl alcohol 10 mg added as a preservative; sodium citrate dehydrates 11 mg; sodium sulfite 1 mg as an antioxidant; water for injection quantity sufficient (q.s.). Citric acid and/or sodium hydroxide may be added for pH adjustments (7.0-8.5). Air in the container is displaced by nitrogen.

The dosage administered is well below the studied amounts of acute toxicity. The intravenous LD50 of dexamethasone sodium phosphate in male mice is 794 mg/kg. The use of dexamethasone sodium phosphate for the treatment of cerebral edema is generally initially a dosage of 10 mg intravenously followed by 4 mg every six hours until the symptoms of cerebral edema subside. Therefore the dosage of dexamethasone in a preferred embodiment is well within the safe limits of its use.

In the present invention, lidocaine has an important synergistic effect in the treatment of migraines when it is included in a pharmaceutical combination with dexamethasone and thiamine. As understood by those having skill in the art, the primary use of local anesthetics, such as lidocaine, is to prevent or relieve pain by reversibly preventing action potential propagation through the inhibition of voltage-gated sodium channels. Lidocaine preferentially binds to open and/or inactivated voltage gated sodium channels.

Thiamine, or vitamin B1, has a synergist effect when combined with lidocaine and dexamethasone for the treatment of migraines in the present invention. Thiamine acts through a number of non-genomic mechanisms, which include regulating protein expression, oxidative stress, inflammation and cellular metabolism. There are no reports of adverse effects of thiamine taken orally, even at dosages of several hundred milligrams per day. Therefore, the recommended dosage of 100 mg of thiamine in the combination treatment with dexamethasone and lidocaine is well below the maximum recommended dosage.

The pharmacologically active compositions of the invention can be produced in accordance with conventional methods for making medicinal agents for administration to patients. The compositions, individually or in combination, are employed in admixture with conventional excipients, i.e. pharmaceutically acceptable organic or inorganic carrier substances suitable for subcutaneous injection, which do not react with the active compositions. Suitable pharmaceutically acceptable carriers include but are not limited to: water, salt solutions, alcohols, gum arabic, vegetable oils, benzyl alcohols, polyethylene glycols, gelatin, carbohydrates, etc. The pharmaceutical preparations can be sterilized and, if desired, mixed with auxiliary agents, e.g. preservatives, stabilizers, emulsifiers, salts for influencing osmotic pressure, buffers, and the like which do not deleteriously react with active agents. They can also be combined with other active agents. Nonetheless, from the description of the above embodiments, other aspects of the invention can be made and/or practiced based on the description provided below and adaptations by those having skill in the art.

In a preferred embodiment, the patient is administered a combination composition of dexamethasone phosphate, thiamine, and lidocaine at least ten treatment sites during a single treatment session (five sites on the left side of the patient's craniofacial region). The patient is administered an amount of dexamethasone phosphate in the range of about 12 mg and 16 mg dexamethasone phosphate, an amount of approximately between 60 mg and 80 mg of lidocaine, and an amount of approximately between 100 mg and 200 mg of thiamine. In a preferred embodiment, the amount of dexamethasone phosphate is 12 mg, an amount of approximately 60 mg lidocaine and an amount of approximately 100 mg thiamine. It is understood that formulations may include the active compositions in the forms of an acceptable salt, solvate, metabolite or racemate. As is readily understood, the ratio of the three compositions in the formulation stay consistent if more or less of the formulation is needed. A ratio of approximately 1 mg dexamethasone to approximately 5 mg of lidocaine to approximately 8.3 mg of thiamine produces an acceptable ratio of individual compositions to the formulation as a whole.

In a preferred embodiment, 1 ml vials are prepared having volumes of 0.3 ml dexamethasone (having 1.2 mg dexamethasone in each 1 ml syringe of the combination composition), 0.1 ml thiamine (having 10 mg thiamine per 1 ml syringe of the combination composition), and 0.6 ml lidocaine (having 6 mg lidocaine per 1 ml syringe of the combination composition). To increase accuracy and consistency of measurements, the 1 ml vials can be aliquoted from a larger container where the compositions could be mixed in proportional volumes and milligrams to the amounts described above.

Nerve branches most commonly receiving administration of the formulation are the first division of the trigeminal nerve (the ophthalmic nerve), the second division of the trigeminal nerve (the maxillary nerve), and the third division of the trigeminal nerve (the mandibular nerve), and greater occipital nerve. The formulation is administered by penetrating the skin of the patient around 90 degrees, and injecting 0.1 ml of the combination formulation each at each individual treatment site, in proximity to the targeted nerve region, which the perfuses to the nerve involved in the migraine pathway. A single treatment session may use approximately 10 mls of the formulation. Total compositions amounts during one treatment session therefore total 12 mg dexamethasone (range of 12 mg-16 mg), 60 mg lidocaine (range of 60 mg-80 mg), and 100 mg thiamine (range of 100 mg-200 mg). Those skilled in the art will recognize that variations of these amounts may be necessary depending the migraine, number of pain locations, and amount of pain suffered by each patient.

If a patient requires additional treatment sessions, the amounts of dexamethasone phosphate, thiamine and lidocaine are preferably reduced to between one-third and one-half of the original amounts used in the first treatment session. Additional treatment sessions are likely only necessary when practitioner did not correctly target the proper nerve location (for example, due to individual having an unusual and unexpected nerve location). Depending on the type and intensity of craniofacial patient experienced by the patient, the practitioner may also change the dosage.

In a preferred embodiment of the treatment method, the composition is administered to several locations and approaches to these locations, during the same treatment session. The practitioner treats one or more of the following craniofacial nerves using one or more of the following approaches: (1) injection in proximity to the frontal nerve with its medial lateral branch that lies over the glabella and forehead, (2) injection in proximity to the supratrochlear nerve over the glabella and forehead and infratrochlear nerve with its rami communicantes at the dorsal aspect of the nose, (3) injection in proximity to the retro-orbital nerve branches associated with the ciliary ganglion, dorsolateral to the optic nerve, approached by puncturing the orbital septum proximally-medially, (4) injection in proximity to the zygomatic branches of the second division (maxillary nerve) approached at the zygomatic bone prominence by involvement of the maxillary nerve using an infraorbital approach, (5) injection in proximity to the nasal mucosa and upper jaw, using an approach through the soft palatine folds, (6) injection in proximity to the infraalveolar branch of the mandibular nerve using an intra-oral approach by puncturing the soft palate in an upward and lateral direction, which may also be used to reach the optic ganglion, (7) injection in proximity to the temporo-parietal muscle and temporal muscle, which are embedded with branches of the first and second trigeminal nerve division (a network of nerve branches), which are treated by several injections into the deeper layer, and then superficial layer of the mentioned muscles from the origin of the muscle tendon to the muscle belly and periphery to the temporo-facial branch of the seventh nerve (facial nerve), (8) injection in proximity to the pterygopalatine ganglion through the masseter muscle and mandibular arc at a 30 degree direction anteriorly and distally (2-3 ml of the formulation may provide appropriate diffusion), (9) injection in proximity to the greater occipital nerve in its ascending and descending branches approached on the base of the semispinal muscle insertion, and one inch distal of the base toward midline; the lesser occipital nerve in its direction of exit through the semispinal muscle lateral to the greater occipital nerve, and 10) injection in proximity to the $2^{nd}$ and $3^{rd}$ spinal nerves in cases of severe neck spasm and pain, which is normally associated with nausea and vomiting.

Some or all of these injection sites and approaches are performed during the same treatment session, and performed bilaterally. Each side of the facial area during the treatment session receives approximately between 20 and 28 total need injections and the treatment session lasts between 60 and 80 minutes. Frequent aspiration is recommended to determine whether the needle has penetrated into a blood vessel, so that the combination formulation can properly perfuse into the nerve and not into a blood vessel.

EXAMPLES

Example 1

Evidence of Curative Effect with Respect to Relapse and Efficacy

A trial was conducted that comprised a treatment method having two different formulations. The first formulation included a combination of dexamethasone and lidocaine. The second formulation included a combination of dexamethasone, lidocaine, and thiamine. The second treatment method was superior to the first treatment method as will be understood from the results and advantages below.

In total, 52 patients were recruited and treated with one of the two formulations. Twelve (12) patients were discarded from study due to non-compliance, address change or no follow-up, leaving 40 patients as part of the study. Notably, all 12 patients discarded from the study had received the first formulation (without thiamine).

Patient Demographics and Co-Morbidities

All patients were White or Hispanic. The age range of the participants was from 12 years old to 87 years old. Patients had migraines from one year to 60 years, with a mean term of migraine headache of 15 years. Ten percent of patients reported a family history of migraines or some type of chronic headache. Thirty-seven (37) patients had an aura associated with their migraine, while three patients were without aura. One patient had a menstrual cycle associated migraine. One patient previously had a hysterosalpingectomy. One patient had lingual and speech loss. One patient had a seizure associate with a migraine. Three patients had concomitant left sided numbness/tingling at the upper and lower extremities. One patient had CCSVI-Multiple Sclerosis. Two patients had status post-"total gastrectomy for neoplastic event" with a prior history of migraine. One patient had Parkinsonism.

Thirty-nine (39) patients had previous experience with medications such as Excedrin, other NSAIDS, different modalities of triptans (injection, nasal spray, tablets), opioids, antiepileptic medications, beta blockers, and alternative natural-herbal supplements. Some patients reported previous attempts at treatment through chiropractic manipulation of the cervical spine. The youngest patient (age 12) was the only patient to report attempted treatments with NSAIDS (ibuprofen). None of the patients underwent neurectomy or any other migraine related surgical procedures. All patients received the same clinical evaluation. Thirty-nine (39) patients presented with extensive diagnostic tests such as Mill or CT-scan of the brain/head.

Combining the results of both treatment methods, of the 40 patients who followed up, 38 (95%) had complete relief. Two (2) patients (5%) reported major relief of migraine symptoms, but with episodic relapsing and remission. The average period of relief without remitting and relapsing has been 15 months, and continues to increase as time progresses and the patients continue to not have any recurring migraine headaches.

First Treatment Group (Formulation without Thiamine)

Of the 40 patients who followed up in the study, 12 patients received treatment with the first formulation of dexamethasone and lidocaine (without thiamine). The longest time reported without migraine recurrence has been over five years, with the average number of months without a migraine being over 39 months. No patients, of the ones who followed up, had any recurrence of migraine headaches. The first formulation had used approximately 20 mg-28 mg dexamethasone per session, and 100 mg-150 mg lidocaine per treatment session for injection in proximity to the nerves and nerve branches described above. No thiamine was used as part of the formulation for patients in the first treatment group.

Second Treatment Group (Formulation with Thiamine)

Of the 40 patients who followed up in the study, 28 patients received the second formulation, which had dexamethasone, lidocaine, and thiamine. For the second treatment group, the amount of dexamethasone was reduced from 20 to 28 mg in the first formulation to 12 mg to 16 mg dexamethasone in the second formulation. The second formulation also reduced the amount of lidocaine from approximately 100 mg to 150 mg in the first formulation to 60 to 80 mg of lidocaine in the second formulation.

Twenty-six (26) of the 28 patients (93%) responded to a single treatment session using the second formulation, while the two remaining patients required a second and third treatment session, which occurred between two days and two months after the initial treatment session. The average number of months without migraine has been eight months. The shorter average number of months of migraine relief compared to the first treatment method is not due to an actual recurrence of migraines, but is due to the fact that the second treatment group started at a later time period compared to the first treatment group, and therefore the follow-up time from treatment to follow-up has been shorter for the second treatment group.

The second treatment group, using the formulation having thiamine in addition to the dexamethasone and lidocaine present the first formulation, had several advantages over the method and formulation not having thiamine, despite both methods having positive effects. The second formulation reduced the higher dosage of lidocaine and dexamethasone initially required in the first formulation. Utilizing the second formulation with thiamine reduced the total required amount of dexamethasone needed from approximately 20 mg-28 mg per session in the first treatment method to approximately 12 mg-16 mg. The second formulation also reduced the amount of lidocaine from approximately 100 mg-150 mg per session to 60 mg-80 mg per session. By reducing the amount of lidocaine needed during the treatment session, patients were able to better tolerate multiple injections through the treatment session compared to the first treatment method where more lidocaine was required. Most patients in the second treatment group also tolerated the nearly 40 injections without interruption, and patients had a more rapid and smoother relief (within 10-36 hours compared to patients in the using the first formulation without thiamine. Lidocaine cream or gel was not required for patients using the second formulation having thiamine. Another advantage of the second formulation and treatment method was the reduced number of non-migrainous (e.g. tension headache) experienced.

While the invention has been described in terms of exemplary embodiments, it is to be understood that the words that have been used are words of description and not of limitation. As is understood by persons of ordinary skill in the art, a variety of modifications can be made without departing from the scope of the invention defined by the following claims, which should be given their fullest, fair scope.

I claim:

1. A method of curing migraine headaches in a patient having recurring migraine headaches comprising:
   administering in a single treatment session to a patient suffering from migraine headaches a pharmaceutical composition having:
      dexamethasone,
      lidocaine, and
      thiamine,
   wherein dexamethasone is administered in an amount of approximately between 12 mg to 16 mg in the single treatment session, thiamine is administered in an amount of approximately between 100 mg to 200 mg in the single treatment session, and lidocaine is administered in an amount of approximately between 60 mg to 80 mg in the single treatment session;
   wherein administering said composition in said single treatment session eliminates recurrence of migraine headaches for a period of at least two years.

2. The method of claim 1, wherein dexamethasone is administered in an amount of about 12 mg in the single treatment session, thiamine is administered in an amount of approximately 100 mg in the single treatment session, and lidocaine is administered in an amount of approximately 60 mg to in the single treatment session.

3. The method of claim 1, wherein the pharmaceutical composition has a ratio of dexamethasone to lidocaine to thiamine in the amount of about 1 mg to 5 mg to 8.3 mg, respectively.

4. The method of claim 3, wherein administering said pharmaceutical composition is characterized as administering dexamethasone, thiamine, and lidocaine to at least ten craniofacial regions.

5. The method of claim 1, wherein said patient having recurring migraines has recurring migraine headaches caused by trigeminal or occipital neuralgia.

6. The method of claim 1, further comprising administering said pharmaceutical composition to ganglia associated peripheral nerves.

7. The method of claim 1, wherein administering said pharmaceutical composition is characterized as administering said composition in proximity to the retro-orbital nerve branch associated with a ciliary ganglion.

8. The method of claim 1, wherein administering said pharmaceutical composition is characterized as administering said pharmaceutical composition to the second and third spinal nerve.

9. The method of claim 1, wherein administering said pharmaceutical composition is characterized as administering said pharmaceutical composition in proximity to the frontal nerve.

10. The method of claim 1, wherein administering said pharmaceutical composition is characterized as administering in said single treatment session, separate injections in proximity to at least one of the following: the frontal nerve, supratrochlear nerve, retro-orbital nerve, zygomatic nerve branches, nasal mucosa, infraalveolar branch of the mandibular nerve, first and second trigeminal nerve division, pterygopalatine ganglion, greater occipital nerve, lesser occipital nerve, second spinal nerve, and third spinal nerve.

11. The method of claim 1, wherein administering said pharmaceutical composition is characterized as administering in said single treatment session, separate injections in proximity to at least three of the following: the frontal nerve, supratrochlear nerve, retro-orbital nerve, zygomatic nerve branches, nasal mucosa, infraalveolar branch of the mandibular nerve, first and second trigeminal nerve division, pterygopalatine ganglion, greater occipital nerve, lesser occipital nerve, second spinal nerve, and third spinal nerve.

12. The method of claim 1, wherein administering said composition is characterized as administering to the patient (1) an amount of dexamethasone, a pharmaceutical acceptable salt, solvate, or racemate thereof, (2) an amount of lidocaine, a pharmaceutically acceptable salt, solvate, or racemate thereof, and (3) an amount of thiamine, a pharmaceutically acceptable salt, solvate, or racemate thereof.

13. The method of claim 1, wherein administering said composition is characterized as administering a ratio of lidocaine to dexamethasone in an amount of about 3.75:1 to 6.67:1 by weight;
   and wherein administering said composition is characterized as administering a ratio of thiamine to dexamethasone an amount of about 6.25:1 to 16.67:1, by weight.

* * * * *